United States Patent

Escher et al.

[11] Patent Number: 5,679,792
[45] Date of Patent: Oct. 21, 1997

[54] DERIVATIVES OF 3-CYCLOHEXYLPROPIONIC ACID, AND THE USE THEREOF IN FERROELECTRIC LIQUID-CRYSTAL MIXTURES

[75] Inventors: Claus Escher, Mühltal, Germany; Gerhard Illian, Tokyo, Japan; Hubert Schlosser, Glashütten/Taunus; Rainer Wingen, Hattersheim am Main, both of Germany

[73] Assignee: Hoechst Aktiengesellschaft, Frankfurt, Germany

[21] Appl. No.: 457,735

[22] Filed: Jun. 1, 1995

Related U.S. Application Data

[63] Continuation of Ser. No. 335,671, Nov. 8, 1994, abandoned, which is a continuation of Ser. No. 5,748, Jan. 19, 1993, abandoned.

[30] Foreign Application Priority Data

Jan. 22, 1992 [DE] Germany .............. 42 01 598.7

[51] Int. Cl.$^6$ .............. C07D 239/34; C07D 213/89; C07D 285/12
[52] U.S. Cl. .............. 544/298; 544/296; 544/315; 544/316; 544/317; 544/318; 544/331; 546/290; 546/314; 546/339; 546/341; 548/136; 548/137
[58] Field of Search .............. 252/299.01, 299.5, 252/299.61; 544/296, 298, 315, 316, 317, 318, 331; 548/136, 137; 546/290, 314, 339, 341

[56] References Cited

U.S. PATENT DOCUMENTS 4,510,069 4/1985 Eidenschink et al. .............. 252/299.61
4,952,699 8/1990 Yong et al. .............. 548/136

FOREIGN PATENT DOCUMENTS 155063 5/1982 Germany .
284 893 11/1990 Germany .
60255-779 5/1984 Japan .
2235192 2/1991 United Kingdom .

OTHER PUBLICATIONS

J.W. Goodby et al., "Ferroelectric Liquid Crystals", pp. 133 and 244 (Philadelphia, 1991).

German Abstract 91-125487/18, published Jun. 9, 1989.

German Abstract 79062 E/38, published Dec. 11, 1980.

Schaefer et al. Chem. Abst. CA116(24):245706b 1990.

*Primary Examiner*—Yogendra N. Gupta
*Attorney, Agent, or Firm*—Curtis, Morris & Safford, P.C.

[57] ABSTRACT

Compounds of formula I

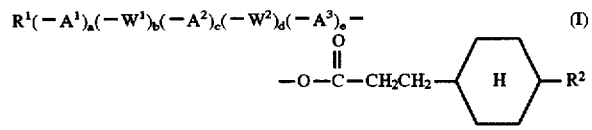

in which $R^1$ and $R^2$ are, for example, an alkyl chain, A is a mesogenic group, and M is a spacer group, are highly suitable as components of liquid-crystal mixtures.

4 Claims, No Drawings

DERIVATIVES OF 3-CYCLOHEXYLPROPIONIC ACID, AND THE USE THEREOF IN FERROELECTRIC LIQUID-CRYSTAL MIXTURES

This application is a continuation of application Ser. No. 08/335,671, filed Nov. 8, 1994, abandoned, which is a continuation of application Ser. No. 08/005,748, filed Jan. 19, 1993, now abandoned.

Particularly in the last decade, liquid crystals have been introduced into various technical areas in which electro-optical and display-device properties are required (for example in watch, calculator and and typewriter displays). These display devices are based on dielectric alignment effects in the nematic, cholesteric and/or smectic phases of the liquid-crystalline compounds, the dielectric anisotropy causing the molecular long axes of the compounds to adopt a preferential alignment in an applied electric field. The usual response times of these display devices are too long for many other potential areas of application of liquid crystals. This disadvantage becomes particularly noticeable if a large number of pixels must be addressed. The production costs of equipment containing relatively large screen areas are then generally too high.

In addition to nematic and cholesteric liquid crystals, optically active smectic (ferroelectric) liquid-crystal phases have also been increasing in importance for some years.

Clark and Lagerwall were able to show that the use of ferroelectric liquid-crystal systems in very thin cells gives electro-optical switching or display elements which, compared with conventional TN ("twisted nematic") cells, have response times which are faster by a factor of up to 1000 (cf., for example, Lagerwall et al., "Ferroelectric Liquid Crystals for Displays", SID Symposium, October Meeting 1985, San Diego, Calif., U.S.A.). Due to these and other favorable properties, for example, the possibility of bistable switching and the contrast, which is virtually independent of the viewing angle, FLCs are in principle suitable for the above-mentioned areas of application, for example via matrix addressing. Due to their high contrast and speed, ferroelectric liquid crystals are also particularly suitable in the area of spatial light modulators (cf., for example, U.Efron in "Spatial Light Modulators and Applications", SPIE Vol. 1150, pp. 46 ff.). However, the speed of ferroelectric liquid-crystal mixtures is generally still not sufficient to drive, for example, high-resolution, fast display elements. It is therefore desirable to find components which increase the response speed of liquid-crystalline mixtures. The invention therefore relates to components which shorten the response time of liquid-crystal mixtures.

Liquid-crystalline derivatives of 3-cyclohexylpropionic acid are described in DD 284 893, and are employed to improve the multiplex ratio in electro-optical components containing nematic liquid-crystal mixtures.

Surprisingly, it has now been found that compounds of the formula I are highly suitable as mixture components for ferroelectric liquid-crystal mixtures (in particular smectic C*). They are readily miscible, have relatively low viscosities—i.e. give short response times—and promote the formation of the nematic (cholesteric) phase, which is advantageous for good alignment in a display, in the temperature region above the smectic C* phase.

The invention therefore relates to compounds of the formula I:

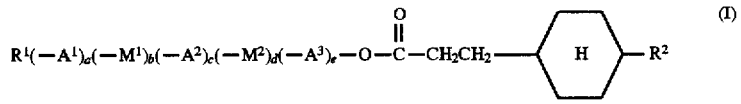

In the formula I, the symbols and indices have the following meanings:

$R^1$ is H or a straight-chain or branched alkyl radical having 1 to 22 carbon atoms (with or without an asymmetric carbon atom) in which, in addition, one or two non-adjacent —$CH_2$— groups may be replaced by —O—, —S—, —CO—, —CO—O—, —O—CO—, —CO—S—, —S—CO—, —O—CO—O—, —CH=CH—, —C≡C—,

or —Si(CH_3)_2— and in which one or more H atoms of the alkyl radical may be replaced by F or Cl, or is one of the following chiral groups:

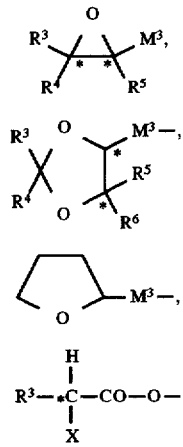

$R^2$, $R^3$, $R^4$, $R^5$ and $R^6$, independently of one another, are H or a straight-chain or branched alkyl radical having 1 to 22 carbon atoms (with or without an asymmetric carbon atom) in which, in addition, one or two non-adjacent —$CH_2$— groups may be replaced by —O—, —S—, —CO—, —O—CO—, —CO—O—, —CO—S—, —S—CO—, —O—CO—O—, —CH=CH—, —C≡C—,

or —Si(CH_3)_2— and in which $R^3$ and $R^4$ together may alternatively be —(CH_2)_4— or —(CH_2)_5— if they are bonded, as substituents, to a dioxolane system, X is —Cl, —Br, —I or —CN, $A^1$, $A^2$ and $A^3$ are identical or different and are 1,4-phenylene in which one or two H atoms may be replaced by F, Cl and/or CN, pyridazine-3,6-diyl, pyrazine-2,5-diyl or pyridine-2,5-diyl or pyrimidine-2,5-diyl in which one or two H atoms may be replaced by F, trans-1,4-cyclohexylene in which one or two H atoms may be replaced by —CN and/or —$CH_3$, 1,3,4-thiadiazole-2,5-diyl, 1,3-dioxane-2,5-diyl, 1,3-dithiane-2,5-diyl, 1,3-thiazole-2,4-diyl, 1,3-thi-azole-2,5-diyl, thiophene-2,4-diyl, thiophene-2,5-diyl, piperazine-1,4-diyl, piperazine- 2,5-diyl, naphthalene-2,6-diyl, bicyclo[2.2.2]octane-1,4-diyl, 1,3-dioxaborinane-2,5-diyl or trans-decalin-2,6-diyl, $M^1$ and $M^2$ are identical or different and are —O—, —S—, —CO—, —CO—O—, —O—CO—, —CO—S—, —S—CO—, —O—CO—O—, —CH$_2$—O—, —O—CH$_2$—, —CH$_2$CH$_2$—, —CH=CH— or —C≡C, $M^3$ is —CH$_2$—O—, —CO—O—, or —CH$_2$—OC(=O)—, a,b,c,d and e are zero or 1, with the proviso that the sum a+c+e is 2 or 3,

* is a chiral center, with the exception of compounds in which the (—A$^1$)$_a$(—M$^1$)$_b$(—A$^2$)$_c$(—M$^2$)$_d$(—A$^3$)$_e$ group has the following meaning:

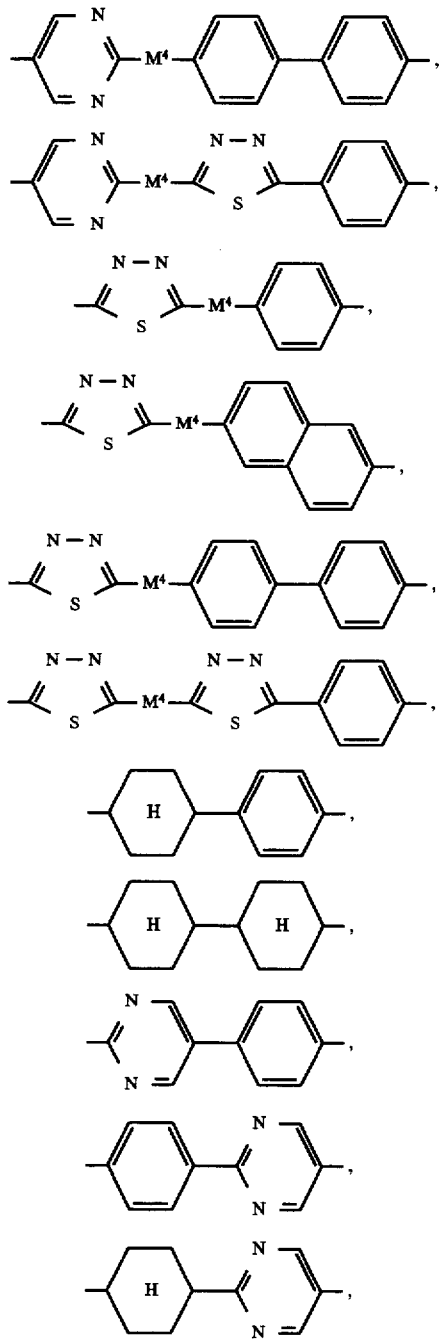

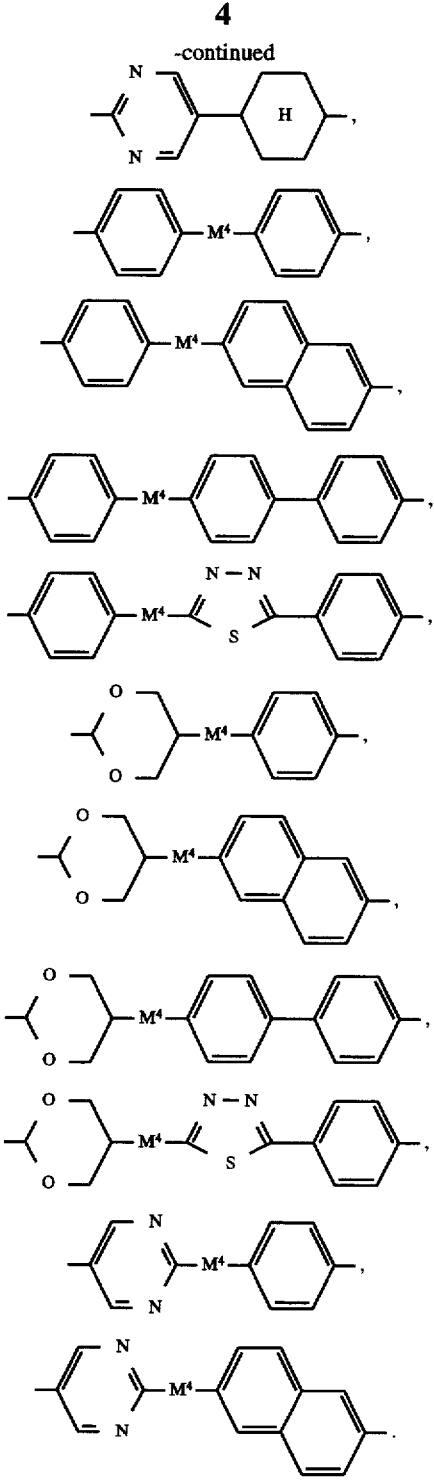

and $M^4$ is —COO—, —OOC— or a single bond.

The invention furthermore relates to the use of the compounds of the formula I, individually or in mixtures, in ferroelectric liquid-crystal mixtures.

Preference is given to compounds of the formula (I), in which the symbols and indices have the following meanings with retention of the said exceptions:

$R^1$ is H or a straight-chain or branched alkyl radical having 1 to 22 carbon atoms (with or without an asymmetric carbon atom) in which, in addition, one or two non-adjacent —CH$_2$— groups may be replaced by —O—, —S—, —CO—, —CO—O—, —O—CO—,

—O—CO—O—, —CH=CH—, —C≡C—,

or —Si(CH₃)₂— or is one of the following chiral groups:

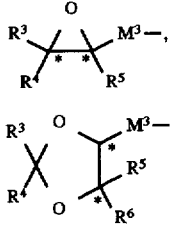

R², R³, R⁴, R⁵ and R⁶, independently of one another, are H or a straight-chain or branched alkyl radical having 1 to 22 carbon atoms (with or without an asymmetric carbon atom) in which, in addition, one or two non-adjacent —CH₂— groups may be replaced by —O—, —S—, —CO—, —O—CO—, —CO—O—, —CO—S—, —S—CO—, —O—CO—O—, —CH=CH—, —C≡C—,

or —Si(CH₃)₂— and in which R³ and R⁴ together may alternatively be —(CH₂)₄— or —(CH₂)₅— if they are bonded, as substituents, to a dioxolane system.

A¹, A² and A³ are identical or different and are 1,4-phenylene, pyrazine-2,5-diyl, pyridazine-3,6-diyl, pyridine-2,5-diyl, pyrimidine-2,5-diyl, trans-1,4-cyclohexylene, 1,3,4-thiadiazole-2,5-diyl, 1,3-dioxane-2,5-diyl, naphthalene-2,6-diyl or bicyclo[2.2.2]octane-1,4-diyl, M¹ and M² are identical or different and are —O—, —CO—, —CO—O—, —O—CO—, —CH₂—O—, —O—CH₂—, —CH₂CH₂—, —CH=CH— or —C≡C—, M³ is —CH₂—O—, —CO—O—, or —CH₂—OC(=O)—.

Particular preference is given to compounds of the formula (I), in which the symbols and indices have the following meanings, with retention of said exceptions:

R¹ is H or a straight-chain or branched alkyl radical having 1 to 22 carbon atoms (with or without an asymmetric carbon atom) in which, in addition, one or two non-adjacent —CH₂— groups may be replaced by —O—, —CO—, —CO—O—, —O—CO—, —CH=CH—, —C≡C—,

or —Si(CH₃)₂— or is the following chiral group:

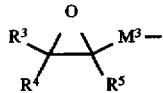

R², R³, R⁴, and R⁵, independently of one another, are H or a straight-chain or branched alkyl radical having 1 to 22 carbon atoms (with or without an asymmetric carbon atom) in which, in addition, one —CH₂— group may be replaced by —O—, A¹, A² and A³ are identical or different and are 1,4-phenylene, pyrazine-2,5-diyl, pyridine-2,5-diyl, pyrimidine-2,5-diyl, trans-1,4-cyclohexylene, 1,3,4-thiadiazole-2,5-diyl, naphthalene-2,6-diyl or 1,3-dioxane-2,5-diyl, M¹ and M² are identical or different and are —O—, —CO—O—, —O—CO—, —CH₂—O—, —O—CH₂—, —CH₂CH₂—, —CH=CH— or —C≡C—, M³ is —CH₂—O—, —CO—O—, or —CH₂—OC(=O)—.

With the retention of the abovementioned exception, very particular preference is given to compounds of the formula I in which R¹ is H or an alkyl radical having 1 to 22 carbon atoms in which one or two non-adjacent —CH₂— groups may be replaced by —O— and/or —CH=CH—, R² is H or an alkyl radical having 1 to 16 carbon atoms, in which, in addition, one —CH₂— group may be replaced by —O—, A¹, A² and A³ are identical or different and are 1,4-phenylene, pyridine-2,5-diyl or pyrimidine-2,5-diyl, M¹ and M² are identical or different and are —O—, —CO—O—, —O—CO—, —CH₂—O— or —O—CH₂—.

The compounds according to the invention can be prepared by methods which are known per se from the literature. 3-cyclohexylpropionic acids can be synthesized either by the process described by Zaschke et al. in DD 155 063 or by the method of Sin et al. (see Tetrahedron Letters, Vol. 29, 1988, pp. 1759–1762). Depending on the preparation process or the nature of the substituent R², 3-cyclohexylpropionic acids having various cis/trans isomer distributions are obtained. The target compounds of the formula (I) can then be prepared by esterifying these 3-cyclohexylpropionic acids using alcohols of the formula R¹(—A¹)ₐ(—M¹)ᵦ(—A²)ᵧ(—M²)ᵨ(—A³)ₑ—OH with the aid of suitable condensation agents, for example carbodiimides (see, for example, Houben-Weyl, Methoden der Organischen Chemie, [Methods of Organic Chemistry], Georg Thieme Verlag, Stuttgart). The compounds of the formula (I) may likewise be obtained as cis/trans mixtures of varying composition. However, suitable measures allow pure cis or trans isomers to be obtained both at the 3-cyclohexylpropionic acid stage and at the compound (I) stage. Both the cis/trans mixtures of (I) and pure cis or trans isomers of (I) can be employed according to the invention.

The compounds of the formula I according to the invention are suitable as components of ferroelectric liquid-crystal mixtures. The LC mixtures may contain from 0.1 to 80% by weight, preferably from 0.5 to 40% by weight, particularly preferably from 1.0 to 20% by weight. The other constituents are preferably selected from known compounds having nematic, cholesteric and/or smectic phases; these include, for example, Schiff bases, biphenyls, terphenyls, phenylcyclohexanes, cyclohexylbiphenyls, N-, S- or O-containing heterocyclic compounds, for example, pyrimidines, cinnamic acid esters, cholesterol esters or various bridged, polycyclic esters of p-alkyl benzoic acids with terminal polar groups.

The use of the compounds according to the invention results in a broadening of the working temperature range in that the SmC* phase is extended to higher temperatures and the melting point is depressed. A particular advantage here is that the (chiral)nematic phase N* is simultaneously retained or even broadened, which results in better alignment properties. A particularly advantageous factor for the suitability in electro-optical switching elements has proven to be the low rotational viscosity, which results in short response times, or equivalently, but of direct relevance for applications in displays, in short pulse durations of the voltage pulses of given amplitude which are necessary for switching.

The mixtures can be used in electro-optical or fully optical elements, for example display elements, switching elements, light modulators, image processing elements, signal processing or generally in the area of nonlinear optics.

The invention is described in greater detail by means of the examples below:

For the ferroelectric liquid-crystal mixtures, the values for the spontaneous polarization $P_s[nC/cm^2]$ and the electrical response time $\tau[\mu s]$ were measured at a temperature of 25° C.

The $P_s$ values were measured by the method of H. Diamant et al. (Rev. Sci. Instr., 28, 30, 1957), using measurement cells with an electrode separation of 10 μm without an alignment layer.

The phase transition temperatures were determined with the aid of a polarizing microscope from the changes in texture which occurred on heating. By contrast, the melting point was determined using a DSC instrument. The phase transition temperatures between the phases
Nematic (N or N*)
Smectic C ($S_c$ or $S_c$*)
Smectic A ($S_A$)
Crystalline (X) are shown in °C. and the values are between the phase designations in the phase sequence.

EXAMPLE 1

2-(4-octyloxyphenyl)pyrimidin-5-yl 3-cyclohexylpropionate 3.00 g (10.0 mmol) of 5-hydroxy-2-(4-octyloxyphenyl) pyrimidin, 1.56 g (10.0 mmol) of 3-cyclohexylpropionic acid, 2.06 g (10.0 mmol) of N,N-dicyclohexylcarbodiimide and 0.1 g of 4-N,N-dimethylaminopyridine in 80 ml of dichloromethane are stirred at room temperature for 18 hours. Insoluble constituents are then filtered off, the mixture is evaporated, and the residue is purified by chromatography (silica gel/dichloromethane) and recrystallization from hexane, giving 2.52 g of 2-(4-octyloxyphenyl) pyrimidin-5-yl 3-cyclohexylpropionate.

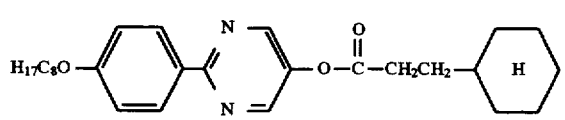

The compound has the phase sequence:

X 66 N 87 I

EXAMPLE 2

4-(5-octyloxypyrimidin-2-yl)phenyl 3-cyclohexylpropionate

The synthesis was carried out analogously to Example 1.

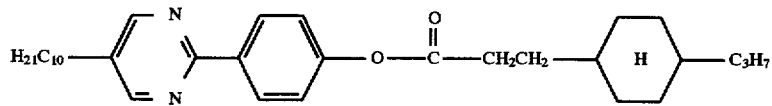

The compound has the phase sequence:

X 97 I

EXAMPLE 3

4-(5-decylpyrimidin-2-yl)phenyl 3-(trans-4-propylcyclohexyl)propionate

The synthesis was carried out analogously to Example 1.

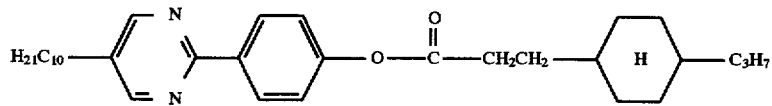

The compound has the phase sequence:
X 88 N 113 I

EXAMPLE 4

4-(5-octyloxypyrimidin-2-yl)phenyl 3-(trans-4-propylcyclohexyl)propionate

The synthesis was carried out analogously to Example 1.

The compound has the phase sequence:
X 72 $S_c$ 82 N 134 I at a cis/trans ratio of 1:3.4
X 78 $S_c$ 86 N 148 I at a cis/trans ratio of 1:46.4
X 80 $S_c$ 81 I at a cis/trans ratio of 1:0.05

EXAMPLE 5

4-(5-octyloxypyrimidin-2-yl)phenyl 3-(trans-4-ethylcyclohexyl)propionate

The synthesis was carried out analogously to Example 1.

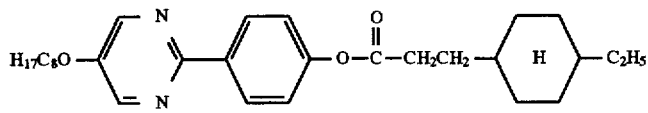

The compound has the phase sequence:
X 68 $S_c$ 82 N 104 I at a cis/trans ratio of 1:1
X 82 $S_c$ 88 N 134 I at a cis/trans ratio of 1:37

EXAMPLE 6

4-(5-decylpyrimidin-2-yl)phenyl 3-(trans-4-hexylcyclohexyl)propionate

The synthesis was carried out analogously to Example 1.

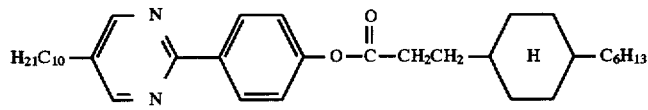

The compound has the phase sequence:
X 69 $S_c$ 73 N 88 I.

EXAMPLE 7

4-(5-octylpyrimidin-2-yl)phenyl 3-(trans-4-hexylcyclohexyl)propionate

The synthesis was carried out analogously to Example 1.

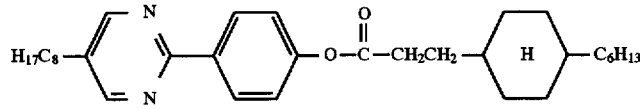

The compound has the phase sequence:
X (48) $S_c$ 47 N 83 I.

EXAMPLE 8

4-[5-(10-undecen-1-oxy)pyrimidin-2-yl]phenyl 3-(trans-4-propylcyclohexyl)propionate The synthesis was carried out analogously to Example 1.

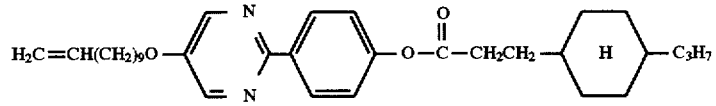

The compound has the phase sequence:

X 43 $S_x$ 45 $S_c$ 107 N 140.5 I at a cis/trans ratio of 1:177

EXAMPLES 9 TO 36

The 3-cyclohexylpropionates shown in the table below were synthesized analogously to Example 1:

| Example No. | Structural formula | Phase sequence |
|---|---|---|
| 9 | H₁₉C₉—[thiadiazole with N-N, S]—[phenyl]—OCCH₂CH₂—[H cyclohexyl]—C₂H₅ | X79S₃93S_c114S_A120I |
| 10 | H₁₃C₆—[pyrimidine N,N]—[phenyl]—OCCH₂CH₂—[H cyclohexyl]—C₂H₅ | X108N119I |
| 11 | H₁₇C₈O—[pyrimidine N,N]—[phenyl]—OCCH₂CH₂—[H cyclohexyl]—C₆H₁₃ | X91S_c81N113I |
| 12 | H₁₉C₉O—[phenyl]—[pyrimidine N,N]—[phenyl]—OCCH₂CH₂—[H cyclohexyl]—C₆H₁₃ | X96S₃161S_c232S_A240I |
| 13 | [cyclohexyl H]—CH₂CH₂CO—[pyrimidine N,N]—[phenyl]—OC—[H cyclohexyl]—C₅H₁₁ | X117X₁130S_A134N214I |
| 14 | H₂C=CH(CH₂)₉O—[pyrimidine N,N]—[phenyl]—OCCH₂CH₂—[H cyclohexyl]—C₂H₅ | X64S_x45S_c102N127I |
| 15 | H₉C₄—[S—S with O]—CH₂O—[pyrimidine N,N]—[phenyl]—OCCH₂CH₂—[H cyclohexyl]—C₂H₅ | X123N142I |
| 16 | H₉C₄—[S—S with O]—CH₂O—[pyrimidine N,N]—[phenyl]—OCCH₂CH₂—[H cyclohexyl]—C₃H₇ | X131N157I |
| 17 | H₂C=CH(CH₂)₄O—[pyrimidine N,N]—[phenyl]—OCCH₂CH₂—[H cyclohexyl]—C₂H₅ | X63S₁78N129I |
| 18 | H₂C=CH(CH₂)₄O—[pyrimidine N,N]—[phenyl]—OCCH₂CH₂—[H cyclohexyl]—C₃H₇ | X78S₁81N147I |
| 19 | H₁₃C₆O—[pyrimidine N,N]—[phenyl]—OCCH₂CH₂—[H cyclohexyl]—C₂H₅ | X66S₁84N139I |
| 20 | H₁₃C₆O—[pyrimidine N,N]—[phenyl]—OCCH₂CH₂—[H cyclohexyl]—C₃H₇ | X84S₁90N156I |

-continued

| Example No. | Structural formula | Phase sequence |
|---|---|---|
| 21 | $H_{17}C_8O$—[pyrimidine]—[phenyl]—OCCH$_2$CH$_2$—[cyclohexyl H]—OC$_4$H$_9$ | X84S$_2$83S$_c$92N142I |
| 22 | $H_{17}C_8O$—[phenyl]—[pyrimidine]—OCCH$_2$CH$_2$—[cyclohexyl H]—C$_2$H$_5$ | X85S$_c$110S$_A$123N150I |
| 23 | $H_9C_4O$—[pyrimidine]—[phenyl]—OCCH$_2$CH$_2$—[cyclohexyl H]—C$_2$H$_5$ | X74S$_x$96N141I |
| 24 | $H_{11}C_5O$—[pyrimidine]—[phenyl]—OCCH$_2$CH$_2$—[cyclohexyl H]—C$_2$H$_5$ | X50X$_1$85S$_1$86N138I |
| 25 | $H_{15}C_7O$—[pyrimidine]—[phenyl]—OCCH$_2$CH$_2$—[cyclohexyl H]—C$_2$H$_5$ | X85S$_1$83N136I |
| 26 | $H_{17}C_8O$—[pyrimidine]—[phenyl]—OCCH$_2$CH$_2$—[cyclohexyl H]—C$_2$H$_5$ | X95N107I |
| 27 | $H_{13}C_6$—[pyrimidine]—[phenyl]—OCCH$_2$CH$_2$—[cyclohexyl H]—C$_2$H$_5$ | X114I |
| 28 | $H_7C_3$—[epoxide S,R]—CO—[pyrimidine]—[phenyl]—OCCH$_2$CH$_2$—[cyclohexyl H]—C$_3$H$_7$ | X$_1$80X$_2$105N181I |
| 29 | $H_7C_3$—[epoxide S,R]—CO—[pyrimidine]—[phenyl]—OCCH$_2$CH$_2$—[cyclohexyl H]—C$_2$H$_5$ | X111N167I |
| 30 | $H_7C_3$—[epoxide R,R]—CO—[pyrimidine]—[phenyl]—OCCH$_2$CH$_2$—[cyclohexyl H]—C$_2$H$_5$ | X124I |
| 31 | [pyrimidine]—[phenyl]—OCCH$_2$CH$_2$—[cyclohexyl H]—C$_2$H$_5$ | X109I |
| 32 | $H_{17}C_8O$—[pyridine]—[pyrimidine]—OCCH$_2$CH$_2$—[cyclohexyl H]—C$_2$H$_5$ | X79S$_A$140I |

| Example No. | Structural formula | Phase sequence |
|---|---|---|
| 33 | 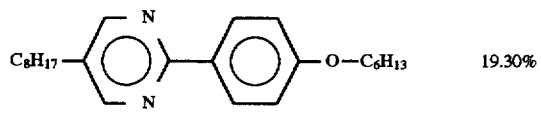 | X86S_B70S_c114N129I |
| 34 | 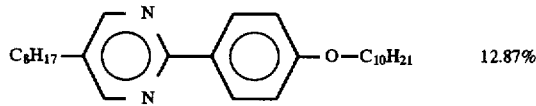 | X96S_B97N105I |
| 35 | 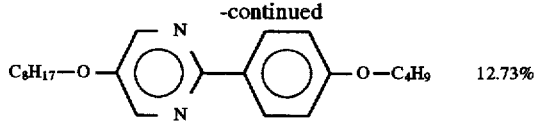 | X105S_B148N199I |
| 36 | 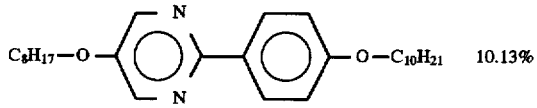 | X74S_c101N131I |

Use Example 1:

The liquid-crystalline base mixture B1 having the following molar composition:

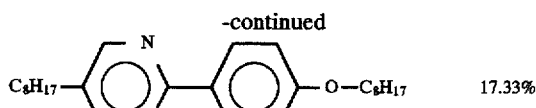  19.30%

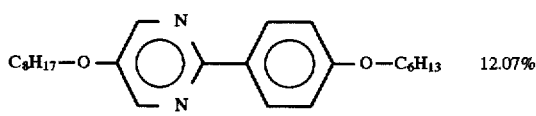  12.87%

-continued

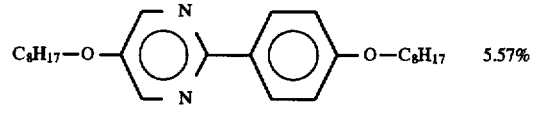  17.33%

(C8H17—O—pyrimidine—phenyl—O—C6H13) 12.07%

(C8H17—O—pyrimidine—phenyl—O—C8H17) 5.57%

-continued

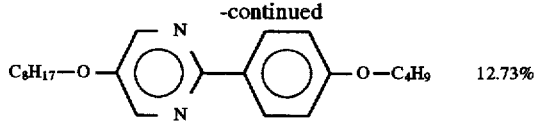  12.73%

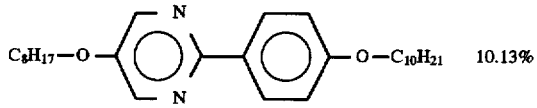  10.13% has the phase sequence:

X 6.5 $S_c$ 63.5$S_A$ 76.8 N 81.5 I.

Addition of 10% of the compound according to the invention

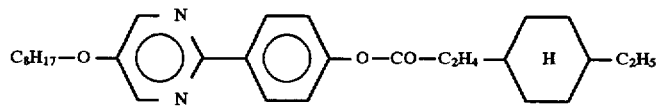

results in the following phase ranges:

X 4 $S_c$ 67 $S_A$ 76.5 N 89 I.

Use Example 2:

The liquid-crystalline base mixture B2 having the following molar composition:

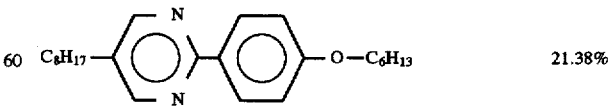  21.38%

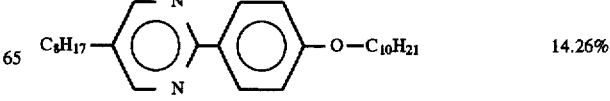  14.26%

-continued
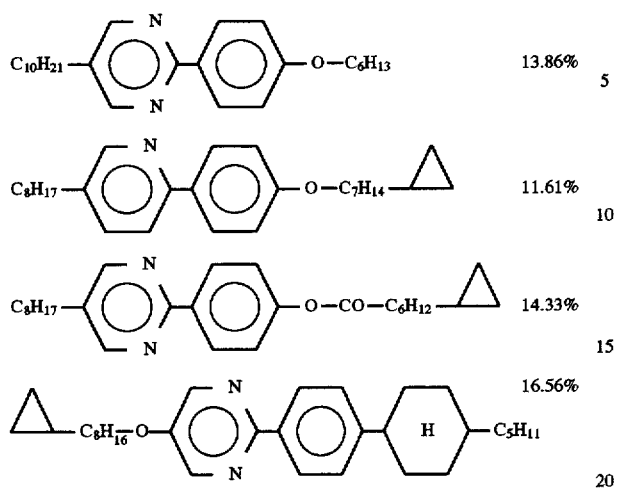
| | |
|---|---|
| | 13.86% |
| | 11.61% |
| | 14.33% |
| | 16.56% |
has the phase sequence:
X 2 S 63 S$_A$ 72 N 82 I.
Addition of 8% of the compound according to the invention
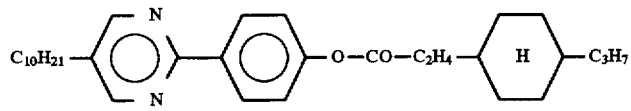
results in the following phase sequence:
X–1 S$_c$ 63.5 S$_A$ 69.5 N 83 I.
Use Example 3:
Addition of the following chiral dopes to the base mixture B1 gave a ferroelectric liquid-crystal mixture:
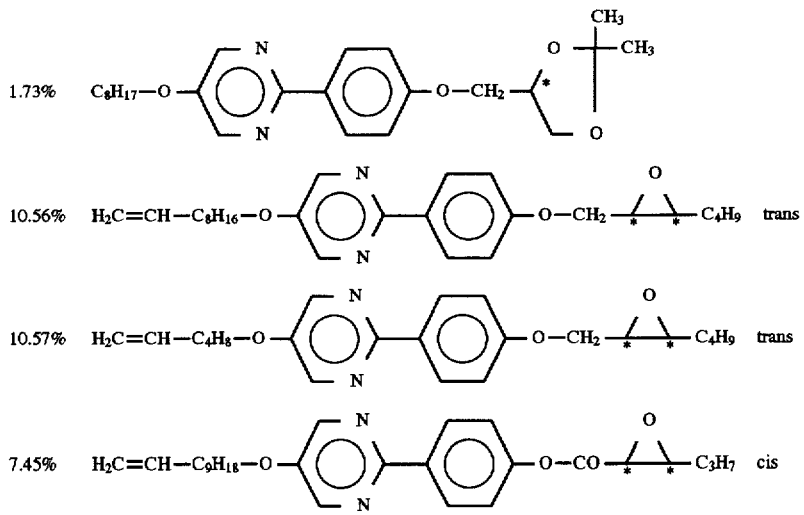

6.97% of the compound according to the invention

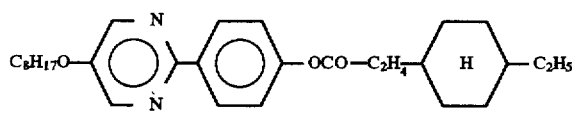

or 12.2% of the comparative compound

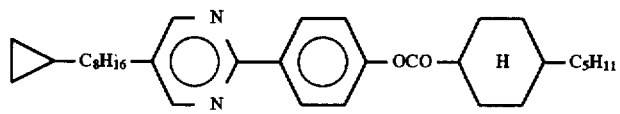

were added to this FLC mixture. The concentration of chiral dopes was adjusted so that it was independent of the addition of the two last-mentioned compounds.

The mixture with the compounds according to the invention has the following phase ranges: $S_c^*$ 60 $S_A$ 78.5 N* 81 I.

It has a spontaneous polarization $P_S$ of 39 nC/cm², a switching angle of 38° and switches on application of an electric pulse of 15 V/µm and a duration of 23 µs. The comparative mixture has the following data:

$S_c^*$ 60 $S_A$ 78 N* 86 I $P_S$=36 nC/cm², switching angle=36°, switching pulse duration necessary=35 µs at an amplitude of 15 V/µm.

Use Example 4:

The molar concentrations shown below of chiral and nonchiral components were added to the base mixture B1:

were then added. The resultant ferroelectric liquid-crystal mixture has the following properties:

Phase ranges X–6 $S_c^*$ 61 $S_A^*$ 80.5 N* 83 I.

$P_s$=35 nC/cm²; switching angle 37°; the pulse duration, necessary for switching, of a bipolar electric switching pulse having an amplitude of 15 V/µm is 26 µs; the contrast in the test cell investigated was 70:1.

TABLE (Use Examples)

| Use Example | Substance Example | Base mixture | Concentration | Phases |
|---|---|---|---|---|
| 5 | 10 | B2 | 92 | X 3 $S_c$ 64 $S_A$ 69 N 86 I |
| 6 | 11 | B2 | 90 | X-9 $S_c$ 58 $S_A$ 66 N 83 I |
| 7 | 14 | B1 | 90 | x 5 $S_c$ 67 $S_A$ 75 N 85 I |
| 8 | 17 | B1 | 87 | X 5 $S_c$ 65 $S_A$ 70 N 86 I |
| 9 | 18 | B1 | 87 | X 5 $S_c$ 65 $S_A$ 66 N 88 I |
| 10 | 19 | B1 | 87 | x 5 $S_c$ 66 $S_A$ 72 N 87 I |
| 11 | 20 | B1 | 87 | X 5 $S_c$ 66 $S_A$ 67 N 89 I |
| 12 | 22 | B1 | 87 | X 5 $S_c$ 68 $S_A$ 79 N 90 I |
| 13 | 23 | B1 | 87 | X 6 $S_c$ 62 $S_A$ 66 N 86 I |
| 14 | 24 | B1 | 87 | X 5 $S_c$ 63 $S_A$ 72 N 87 I |

10.56% 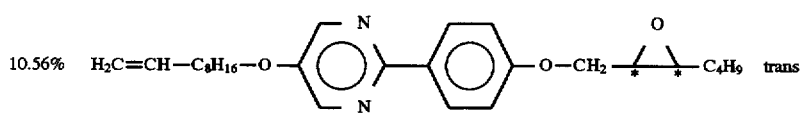 trans 10.57% 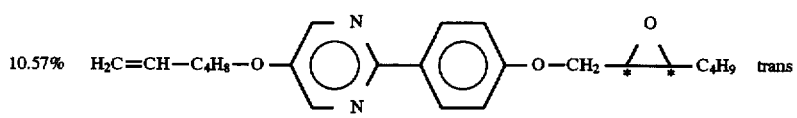 trans 7.45% 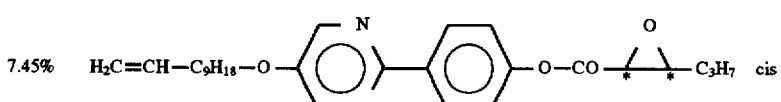 cis 3.57% 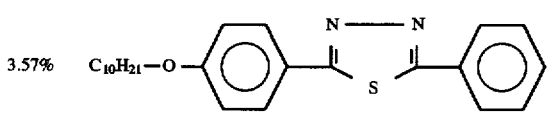

3.57% 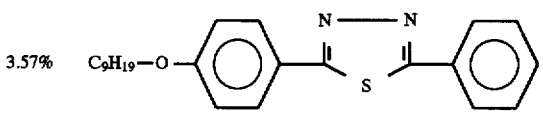

6.43% of the compound according to the invention

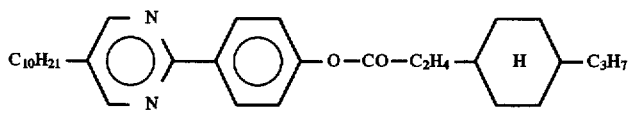

TABLE-continued

(Use Examples)

| Use Example | Substance Example | Base mixture | Concentration | Phases |
|---|---|---|---|---|
| 15 | 25 | B1 | 87 | X 6 $S_c$ 66 $S_A$ 74 N 91 I |
| 16 | 26 | B1 | 87 | X 4 $S_c$ 64 $S_A$ 70 N 88 I |
| 17 | 32 | B1 | 93 | X 4 $S_c$ 81 N 86 I |
| 18 | 34 | E1 | 90 | X 3 $S_c$ 64 $S_A$ 75 N 84 I |
| 19 | 35 | B1 | 90 | X 4 $S_c$ 67 $S_A$ 72 N 91 I |
| 20 | 36 | B1 | 87 | X 3 $S_c$ 69 $S_A$ 77 N 88 I |

It can be seen from the above table that the compounds according to the invention broaden the temperature ranges of the smectic C and nematic phases and can thus advantageously be employed in mixtures.

Use Example 21:

The molar concentrations shown below of chiral and non-chiral components are added to the base mixture B1:

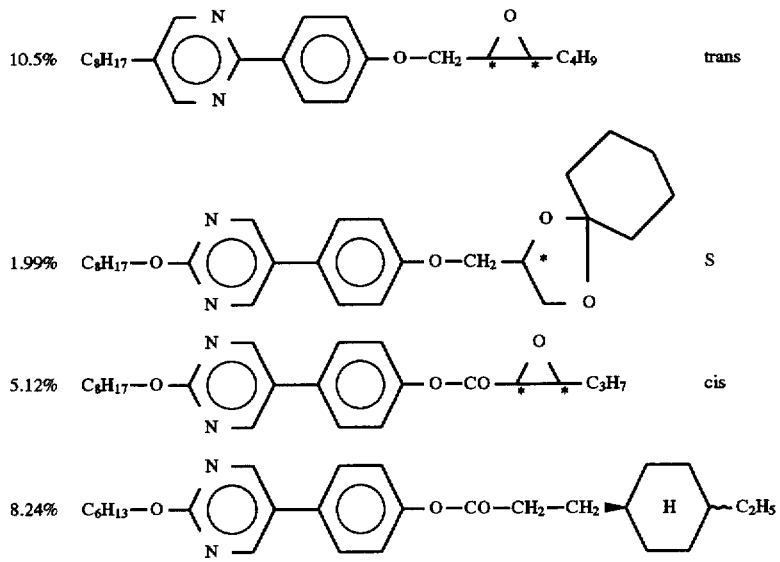

The mixture has the phase sequence:

X–2° $S_c$* 62° $S_A$ 68° N* 80° I

The spontaneous polarization is 35 nC/cm².

We claim:

1. A ferroelectric liquid crystal mixture, comprising at least one compound of formula I

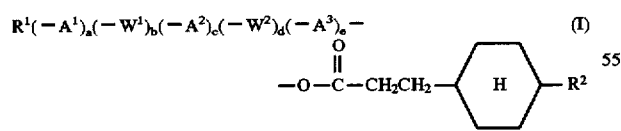

in which the symbols and indices have the following meanings:

$R^1$ is H or a straight-chain or branched alkyl radical having 1 to 22 carbon atoms (with or without an asymmetric carbon atom) in which, in addition, one or two non-adjacent —CH$_2$— groups may be replaced by —O—, —CO—O—, —O—CO—, or —Si(CH$_3$)$_2$— and in which one or more H atoms of the alkyl radical may be replaced by F, or is one of the following chiral groups:

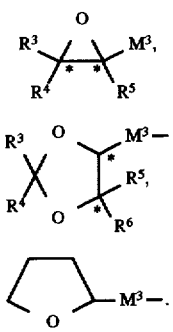

$R^2$ is H;

$R^3$, $R^4$, $R^5$ and $R^6$, independently or one another, are H or a straight-chain or branched alkyl radical having 1 to 22 carbon atoms (with or without an asymmetric carbon atom) in which $R^3$ and $R^4$ together may alternatively be —(CH$_2$)$_4$— or —(CH$_2$)$_5$— if they are bonded, as substituents, to a dioxolane system, $A^1$, $A^2$ and $A^3$ are identical or different and are 1,4-phenylene in which one or two H atoms may be replaced by F, pyridine-2,5-diyl or pyrimidine-2,5-diyl in which one or two H atoms may be replaced by F, trans-1,4-cyclohexylene in which one or two H atoms may be replaced by —CN and/or —CH$_3$, or 1,3,4-thiadiazole-2,5-diyl, $M^1$ and $M^2$ are identical or different and are —CO—O—, —O—CO—, or —CH$_2$CH$_2$—, $M^3$ is —CH$_2$—O—, —CO—O—, —CH$_2$—OC(=O)— or a single bond, a, b, c, d and e are zero or 1, with the proviso that the sum a+c+e is 2 or 3, and

* is a chiral center.

2. A ferroelectric liquid crystal mixture as claimed in claim 1, where the symbols and indices have the following meanings:

$R^1$ is H or a straight-chain or branched alkyl radical having 1 to 22 carbon atoms (with or without an asymmetric carbon atom) in which, in addition, one or two non-adjacent —CH$_2$— groups may be replaced by —O—, —CO—O—, —O—CO—,

or —Si(CH$_3$)$_2$— or is one of the following chiral groups

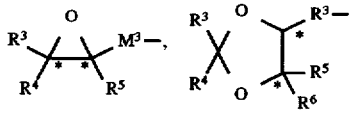

$R^2$ is H;

$R^3$, $R^4$, $R^5$ and $R^6$, independently of one another, are H, or a straight-chain or branched alkyl radical having 1 to 22 carbon atoms (with or without an asymmetric carbon atom) in which $R^3$ and $R^4$ together may alternatively be —(CH$_2$)$_4$— or —(CH$_2$)$_5$— if they are bonded, as substituents, to a dioxolane system, $A^1$, $A^2$ and $A^3$ are identical or different and are 1,4-phenylene, pyridine-2,5-diyl, pyrimidine-2,5-diyl, trans-1,4-cyclohexylene, or 1,3,4-thiadiazole-2,5-diyl, $M^1$ and $M^2$ are identical or different and are —CO—O—, —O—CO—, or —CH$_2$CH$_2$—, $M^3$ is —CH$_2$—O—, —CO—O—, or a single bond.

3. A ferroelectric liquid crystal mixture as claimed in claim 1, where the symbols and indices have the following meanings:

$R^1$ is H or a straight-chain or branched alkyl radical having 1 to 22 carbon atoms (with or without an asymmetric carbon atom) in which, in addition, one or two non-adjacent —CH$_2$— groups may be replaced by —O—, —CO—O—, —O—CO—,

or —Si(CH$_3$)$_2$— or is the following chiral group:

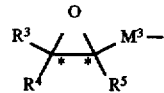

$R^2$ is H;

$R^3$, $R^4$, and $R^5$, independently of one another, are H or a straight-chain or branched alkyl radical having 1 to 22 carbon atoms (with or without an asymmetric carbon atom), $A^1$, $A^2$ and $A^3$ are identical or different and are 1,4-phenylene, pyridine-2,5-diyl, pyrimidine-2,5-diyl, trans-1,4-cyclohexylene, or 1,3,4-thiadiazole-2,5-diyl, $M^1$ and $M^2$ are identical or different and are —CO—O—, —O—CO—, or —CH$_2$CH$_2$—, $M^3$ is —CH$_2$—O—, —CO—O—, or a single bond.

4. A ferroelectric liquid crystal mixture as claimed in claim 1, wherein $R^1$ is H or an alkyl radical having 1 to 22 carbon atoms in which one or two non-adjacent —CH$_2$— groups may be replaced by —O—, $R^2$ is H;

$A^1$, $A^2$ and $A^3$ are identical or different and are 1,4-phenylene, pyridine-2,5-diyl or pyrimidine-2,5-diyl, $M^1$ and $M^2$ are identical or different and are —CO—O—, or —O—CO—.

* * * * *